`US011827914B2`

(12) United States Patent
Gao et al.

(10) Patent No.: US 11,827,914 B2
(45) Date of Patent: Nov. 28, 2023

(54) PLANT UREASE-CONTAINING SOIL SOLIDIFICATION AGENT AND ZERO-WASTE PRODUCTION PROCESS THEREOF

(71) Applicant: HOHAI UNIVERSITY, Jiangsu (CN)

(72) Inventors: Yufeng Gao, Jiangsu (CN); Boyang Yan, Jiangsu (CN); Shuang Shu, Jiangsu (CN); Yi Zhang, Jiangsu (CN); Bin Ge, Jiangsu (CN); Zhitao Ye, Jiangsu (CN)

(73) Assignee: HOHAI UNIVERSITY, Jiangsu (CN)

( * ) Notice: Subject to any disclaimer, the term of this patent is extended or adjusted under 35 U.S.C. 154(b) by 119 days.

(21) Appl. No.: 17/563,118

(22) Filed: Dec. 28, 2021

(65) Prior Publication Data
US 2022/0204962 A1 Jun. 30, 2022

(30) Foreign Application Priority Data
Dec. 31, 2020 (CN) .......................... 202011636114.7

(51) Int. Cl.
*C12N 9/80* (2006.01)
*E02D 3/12* (2006.01)

(52) U.S. Cl.
CPC ................. *C12N 9/80* (2013.01); *E02D 3/12* (2013.01); *C12Y 305/01005* (2013.01)

(58) Field of Classification Search
CPC .... C12N 9/80; C12Y 3505/01005; E02D 3/12
See application file for complete search history.

(56) References Cited

U.S. PATENT DOCUMENTS 4,715,746 A * 12/1987 Mann ................... C09K 8/5086
507/926
8,210,776 B2 * 7/2012 Darson-Balleur ..........................
C04B 41/4803
405/302.6

(Continued)

FOREIGN PATENT DOCUMENTS

CN 109097061 12/2018
CN 109356176 2/2019

OTHER PUBLICATIONS

Dilrukshi et al.; "Soil improvement using plant-derived urease-induced calcium carbonate precipitation" Aug. 2018; All (Year: 2018).*

(Continued)

*Primary Examiner* — Benjamin F Fiorello
(74) *Attorney, Agent, or Firm* — JCIP GLOBAL INC.

(57) ABSTRACT

The present invention belongs to the technical field of rock and soil reinforcement, and specifically relates to a plant urease-containing soil solidification agent and a zero-waste production process thereof. A crudely-purified plant urease solution includes a large amount of irrelevant proteins, which seriously affects the treatment effect of the soil solidification agent, makes it impossible to achieve an expected construction purpose, and also causes serious waste and environmental pollution. In the present invention, a common plant urease extraction method on the market is optimized to significantly reduce a protein concentration in a plant urease solution, greatly improve the infiltration performance of a plant urease-containing soil solidification agent, and broaden an application range of such a soil solidification agent.

1 Claim, 7 Drawing Sheets

(56) References Cited

U.S. PATENT DOCUMENTS

| | | | |
|---|---|---|---|
| 10,563,233 B2* | 2/2020 | Kavazanjian .. | C12Y 305/01005 |
| 11,299,441 B2* | 4/2022 | Kiiski ................ | C05G 5/30 |
| 2002/0156337 A1* | 10/2002 | Jensen ................ | B09C 1/08 |
| | | | 588/316 |
| 2018/0272396 A1* | 9/2018 | Farmer .............. | C07K 14/32 |

OTHER PUBLICATIONS

Zhang Tiejun et al., "Study on the Extraction and Factors Affecting Enzyme Activity of Urease from Soybean Dregs", Current Biotechnology, May 2017, submit with English abstract, pp. 253-257.

* cited by examiner

PLANT UREASE-CONTAINING SOIL SOLIDIFICATION AGENT AND ZERO-WASTE PRODUCTION PROCESS THEREOF

CROSS-REFERENCE TO RELATED APPLICATION

The present application is based on and claims the priority benefits of China application No. 202011636114.7, filed on Dec. 31, 2020. The entirety of the above-mentioned patent application is hereby incorporated by reference herein and made a part of this specification.

BACKGROUND

Technical Field

The present invention belongs to the technical field of rock and soil reinforcement, and specifically relates to a plant urease-containing soil solidification agent and a zero-waste production process thereof.

Description of Related Art

Enzyme induced carbonate precipitation (EICP) is an emerging technology in the field of geotechnical engineering. According to the EICP technology, urea, a calcium source, and a commercial urease are added to soil at a predetermined ratio to induce the formation of calcium carbonate with cementing capacity, such that soil particles are cemented together, thereby achieving soil improvement. At present, a large number of experimental studies have been conducted on the EICP technology based on commercial urease by scholars and experts at home and abroad. It has been confirmed that the EICP technology can effectively enhance the strength of soil, improve the permeability of soil, and enhance the ability of soil to resist wind and water erosion.

Due to the difficult and high-cost purification of commercial urease, the EICP technology is less economical and is currently at a disadvantage in engineering. In order to save costs, plant urease has been successfully extracted from some plant tissues and organs (soybeans, sword beans, watermelon seeds, etc.) by many scholars, and also has the ability to decompose urea into carbonate. Many subsequent studies have proved that the plant urease can be a relatively perfect substitute for commercial urease in an EICP experiment. In addition, a large number of experiments have proved that the EICP technology based on plant urease is easy and rapid in construction and economical, which has been used in various engineering fields such as anti-liquefaction treatment for foundations, wind-break and sand-fixation in deserts, and side slope reinforcement, and has achieved good effects.

However, the EICP technology based on plant urease also needs to be improved. For example, the existing purification of plant urease is an extremely-simple crude purification, so the resulting substances purified from a plant not only include urease, but also include other substances irrelevant to the reaction process, such proteins and lipids. Among these irrelevant substances, proteins have the greatest adverse impact, because an added inorganic salt can cause the proteins in a plant urease solution to undergo a series of complex reactions, and eventually block voids among soil particles, which will hinder the infiltration and further reinforcement of a solidification agent to soil. In order to reduce the influence of the proteins and other irrelevant substances on an EICP reaction process, a new technology is urgently needed to improve the existing methods for extracting plant urease, which can remove most of proteins and other irrelevant impurities in the plant urease solution with no influence or little influence on the activity of plant urease, thereby improving the treatment effect of the EICP technology based on plant urease. Moreover, the removed proteins have extremely high economic value, and if the proteins can be reused, the cost of the EICP technology based on plant urease can be further reduced.

SUMMARY

Technical problem to be solved by the present invention: In view of the shortcomings in the prior art, the present invention provides a pretreated plant urease-containing soil solidification agent, which can address soil clogging and other problems caused by a too high protein content in the conventional plant urease-containing solidification agent, and thus has an improved permeability. In the present invention, bean dregs and organic matters such as irrelevant soybean protein separated through pretreatment are collected and reused to produce by-products such as soy products, which can further reduce the economic cost. Moreover, the present invention also provides a zero-waste production process for the plant urease-containing soil solidification agent, wherein the optimal pretreatment plan can be determined for raw materials of different types and batches to obtain the most effective soil solidification agent, and all wastes are recycled to reduce the pretreatment cost and completely avoid waste pollution.

In order to achieve the above objectives, the present invention adopts the following technical solutions.

A plant urease-containing soil solidification agent and a zero-waste production process thereof are provided.

The plant urease-containing soil solidification agent is prepared from a pretreated plant urease solution and an inorganic treatment solution in a volume ratio of 4:1 to 1:4.

Further, the inorganic treatment solution is a solution prepared by mixing a 0.1 to 3 mol/L of urea solution with a 0.1 to 3 mol/L of calcium salt solution in equal volumes to obtain a resulting mixture, and thoroughly stirring the resulting mixture.

Further, the pretreated plant urease solution is a plant urease solution prepared by a zero-waste production process with proteins removed according to an optimal pretreatment plan.

Further, the calcium salt is one or more selected from the group consisting of calcium chloride, calcium nitrate, calcium acetate, and calcium formate.

A zero-waste production process of a plant urease-containing soil solidification agent is provided, mainly including the following steps.

Step 1, Preparation of a Conventional Plant Urease Solution

Drying an appropriate amount of beans in an oven at 60° C. for 2 h, crushing the dried beans in a crusher and sieving the crushed beans through a 100-mesh sieve to obtain a bean powder, and collecting and storing the bean powder at a ventilated place.

Weighing and dissolving an appropriate amount of the bean powder in deionized water to obtain a first resulting mixture, and thoroughly stirring the first resulting mixture to obtain a 10 to 200 g/L of bean powder solution; centrifuging the bean powder solution for 15 min at 4° C. and 3,000 r/min with a KDC-2046 low-speed refrigerated centrifuge; and filtering the centrifuged bean powder solution to collect a solid residue A and a filtrate separately, where the filtrate is the conventional plant urease solution and the solid residue A is a bean dreg A.

Step 2, Pretreatment of the Conventional Plant Urease Solution

Refrigerating the conventional plant urease solution obtained in the step 1 for 12 h in a 5° C. environment, and taking the conventional plant urease solution out for later use before the pretreatment is performed; preparing a plurality of beakers (7 to 9), and numbering the beakers for later use; adding the conventional plant urease solution in an equal volume of 100 to 200 mL to each of the beakers, putting a magnetic rotor in each of the beakers, and placing the beakers on a magnetic stirrer for continuous stirring to ensure homogeneity of the conventional plant urease solution; taking an appropriate amount of a pretreatment reagent (calcium chloride, magnesium chloride, or calcium sulfate) into an oven at 60° C. for 12 h to form agglomerates, and taking the agglomerates out from the oven and grinding the agglomerates into a powder for later use.

According to an initial concentration of the conventional plant urease solution, selecting a corresponding pretreatment reagent concentration gradient plan; weighing an appropriate amount of the pretreatment reagent and adding the pretreatment reagent to each of the plurality of beakers, stirring a resulting solution at a low speed for 5 min, and stopping the magnetic stirrer to let the solution stand for 5 min; when the solution undergoes an obvious stratification and an upper supernatant is clear, pouring the resulting solution into a centrifuge bottle, and centrifuging the resulting solution for 15 min at 4° C. and 3,000 r/min with the KDC-2046 low-speed refrigerated centrifuge; filtering the resulting solution after centrifugation to collect a clear solution and a solid residue B separately, where the clear solution is a pretreated plant urease solution and the solid residue B is organic matters such as a soybean protein separated.

Where according to the concentration of the conventional plant urease solution prepared in the step 1 (10 to 200 g/L), the corresponding pretreatment reagent concentration gradient plan (0.0005 to 0.15 mol/L) is selected to pretreat the conventional plant urease solution (a pretreatment reagent concentration gradient of 0.0005 to 0.0075 mol/L is used for the conventional plant urease solution with a concentration of 10 g/L, and a pretreatment reagent concentration gradient of 0.01 to 0.15 mol/L is used for the conventional plant urease solution with a concentration of 200 g/L).

Step 3, Determination of an Optimal Pretreatment Plan

Collecting the clear pretreated plant urease solutions from multiple different pretreatment plans obtained in the step 2, and sorting the clear pretreated plant urease solutions according to numbers of the beakers; as performances of the clear pretreated plant urease solutions represent pretreatment effects of the multiple different pretreatment plans on the conventional plant urease solution with a predetermined concentration, determining parameters such as activity and protein content for each of the clear pretreated plant urease solutions, and analyzing the pretreatment effects of the multiple different pretreatment plans to determine the optimal pretreatment plan for the conventional plant urease solution with the predetermined concentration.

Where each of the pretreated plant urease solutions is tested; a biuret staining method is used to test the protein content for each of the pretreated plant urease solutions, a conductivity method is used to test the urease activity for each of the pretreated plant urease solutions, and test results are analyzed statistically; with each of an activity residual rate S and a protein utilization rate K for each of the pretreated plant urease solutions as y-coordinate and an addition concentration of the pretreatment reagent as x-coordinate, curves are plotted; values of the activity residual rate S and the protein utilization rate K are comprehensively analyzed, and an optimal pretreatment reagent concentration is selected according to a selection principle, which is the optimal pretreatment plan; and the pretreated plant urease solution obtained from the optimal pretreatment plan is an optimal pretreated plant urease solution at the concentration.

Wherein in the biuret staining method, 1 mL of each of standard protein solutions at different concentrations is prepared, 4 mL of a biuret reagent is added, and a resulting mixture is well shaken, placed at room temperature for 30 min, and subjected to colorimetric assay at 540 nm using a spectrophotometer; a protein standard curve is plotted according to assay results; and 2 to 3 test tubes are prepared, and a protein concentration of each of the pretreated plant urease solutions is determined by the same method as above.

In the conductivity method, 3 mL of each of the clear pretreated plant urease solutions is taken and added with 27 mL of a 1.11 mol/L urea solution, and the conductivity change of a resulting mixture is determined every 5 min at room temperature using a conductivity meter; the conductivity change is continuously determined 3 times, and an average is taken; the plant urease hydrolyzes urea to produce carbonate ions and ammonium ions, and the ion change in the solution will cause the conductivity change, the conductivity change in the solution is positively correlated with the amount of urea hydrolyzed, so the amount of urea hydrolyzed per unit time can be used as an index for measuring the plant urease activity.

Step 4, Preparation of the Soil Solidification Agent

Preparation of an inorganic treatment solution: mixing a 0.1 to 3 mol/L urea solution with a 0.1 to 3 mol/L of calcium salt solution in equal volumes to obtain a second resulting mixture, and thoroughly stirring the second resulting mixture to obtain the inorganic treatment solution.

Preparation of the soil solidification agent: mixing the optimal pretreated plant urease solution with the inorganic treatment solution in a volume ratio of 4:1 to 1:4 to obtain a third resulting mixture, and thoroughly stirring the third resulting mixture to obtain the soil solidification agent.

Step 5. Reuse of Wastes

Dissolving the bean dreg A obtained in the step 1 with deionized water in an identical volume as that used in the step 1, and stirring a resulting mixture with a magnetic mixer for 30 to 40 min and filtering the mixture through a prewetted white gauze; vigorously squeezing the white gauze to collect a filtrate as much as possible, which is a soybean protein solution A, and collect a filter residue, which is a bean dreg B.

Dissolving the solid residue B obtained in the step 2 with deionized water in an identical volume as that used in the step 1, stirring a resulting mixture with a magnetic mixer for 1 to 3 h until the solid residue is almost completely dissolved, and stopping the stirring; and filtering a resulting solution to collect a filtrate which is a soybean protein solution B.

Mixing the soybean protein solution A and the soybean protein solution B to obtain a soybean protein solution C, where the soybean protein solution C includes the proteins that can be reused throughout the process, which can be made into tofu, dried tofu, and other by-products by conventional production processes.

The bean dreg B can be made into a bean meal by a conventional production process.

The beans in the step 1 refer to urease-rich seeds of a leguminous plant, including but not limited to soybeans and sword beans.

The pretreatment reagent in the step 2 refers to a strong electrolyte that can destroy an ionization balance of a protein and cause coagulation and precipitation when added at a very small amount, and the pretreatment reagent includes, but is not limited to, calcium chloride, magnesium chloride, and calcium sulfate.

In the step 2, in order to determine the optimal pretreatment plan for the conventional plant urease solution with the predetermined concentration, a pretreatment reagent concentration gradient is preset; and as a concentration gradient reference standard, a pretreatment reagent concentration gradient of $5 \times 10^{-5}$ mol/L to $7.5 \times 10^{-4}$ mol/L is used for a 1 g/L conventional plant urease solution. According to actual accuracy requirements, a few or multiple different concentration groups may be set. It should be noted that the reference standard is merely a reference value, and an actual set concentration can be lower or higher than the reference standard.

In the step 2, the pretreated plant urease solution is centrifuged with a low-speed refrigerated centrifuge to separate the pretreated plant urease solution from a precipitated soybean protein. However, in an actual construction process, centrifugation may be impossible, in which case, filtration can also achieve the solid-liquid separation to some extent, but the efficiency and effect are reduced to some extent.

In the step 3, it is possible to test the urease activity for each of the pretreated plant urease solutions with the conductivity method, because a total amount of the pretreatment reagent added to the conventional plant urease solution is generally small and a conductivity of the pretreatment reagent in the solution is low, which will not interfere with a normal test reading of the conductivity meter. If the conventional plant urease solution has a very high concentration, the pretreatment reagent needs to be added at a high concentration, which will reduce the accuracy of the conductivity method. In this case, the Nessler's reagent is recommended to determine ammonia nitrogen, thereby determining a urea decomposition rate and evaluating the activity of the pretreated plant urease solution.

In the step 3, the standard protein solutions at the different concentrations are prepared as follows: a standard crystalline bovine serum albumin (BSA) or standard casein is used to prepare a 10 mg/ml standard protein solution, and a purity of the 10 mg/ml standard protein solution is corrected by setting A280 of 1 mg/ml BSA to 0.66; 0 ml, 0.2 ml, 0.4 ml, 0.6 ml, 0.8 ml, and 1.0 ml of the standard protein solution are added to 6 colorimetric tubes, respectively, with making up to 1 ml with water, such that the standard protein solutions at concentrations of 0 mg/ml, 2 mg/ml, 4 mg/ml, 6 mg/ml, 8 mg/ml, and 10 mg/ml are obtained.

In the step 3, the protein concentration of each of the pretreated plant urease solutions is determined as follows: according to a specified method, an OD value of each of the standard protein solutions is determined with the spectrophotometer, and the obtained OD values are mapped to a standard protein curve to obtain protein concentrations of different solutions.

In the step 3, the activity residual rate S of the pretreated plant urease solution refers to a ratio of a residual activity of the pretreated plant urease solution to an initial activity of the conventional plant urease solution without pretreatment; and the protein utilization rate K of the pretreated plant urease solution refers to a ratio of a concentration of proteins separated from the pretreated plant urease solution that can be secondarily utilized to an initial protein concentration of the conventional plant urease solution without pretreatment.

In the step 3, according to the selection principle, pretreatment groups at different concentrations are preset to plot active protein curves, and based on the activity residual rate $S \geq 70\%$, a pretreatment group corresponding to a maximum of the protein utilization rate $K_{max}$ is selected as the optimal pretreatment plan.

The calcium salt in the step 4 refers to a chemical substance that can provide a free calcium source for a reaction system; and the calcium salt includes, but is not limited to, calcium chloride, calcium acetate, and calcium nitrate.

Beneficial effects of the present invention: In the present invention, a common plant urease-containing solidification agent on the market is optimized to significantly reduce a protein concentration in a plant urease solution, avoid the widespread clogging issue of a plant urease-containing soil solidification agent to some extent, greatly improve the infiltration performance of a plant urease-containing soil solidification agent, and broaden an application range of such a soil solidification agent. In the present invention, the separated soybean protein, the remaining bean dregs, and other solid wastes are secondarily used to prepare by-products with economic benefits, which greatly reduces the cost of the soil solidification agent. The present invention also realizes a zero-waste production process, that is, no waste is generated during a soil solidification agent production process, and there is no environmental stress.

BRIEF DESCRIPTION OF THE DRAWINGS

FIG. 8 (a) shows a surface state of a sample sprayed with the 40 g/L of pretreated plant urease solution twice, and FIG. 8 (b) shows a surface state of a sample sprayed with the 40 g/L of conventional plant urease solution twice.

FIG. 9 (a) shows a surface state of a sample sprayed with the 40 g/L of pretreated plant urease solution 4 times, and FIG. 9 (b) shows a surface state of a sample sprayed with the 40 g/L of conventional plant urease solution 4 times.

DESCRIPTION OF THE EMBODIMENTS

The specific implementation of the present invention is further described in detail below through the description of examples, which is intended to help those skilled in the art understand and implement the concept and technical solutions of the present invention more completely, accurately and deeply.

A zero-waste production process of a plant urease-containing soil solidification agent according to the present invention includes the following steps.

An appropriate amount of beans is dried in an oven at 60° C. for 2 h, then crushed in a crusher and sieved through a 100-mesh sieve to obtain a bean powder, and the bean powder is collected and stored at a ventilated place; an appropriate amount of the bean powder is weighed and dissolved in deionized water, and a resulting mixture is thoroughly stirred to obtain a 10 g/L to 200 g/L bean powder solution; the bean powder solution is centrifuged for 15 min at 4° C. and 3,000 r/min with a KDC-2046 low-speed refrigerated centrifuge to obtain a resulting mixture; and the resulting mixture after the centrifugation is filtered, and a solid residue and a filtrate are collected, separately, wherein the filtrate is the conventional plant urease solution and the solid residue is a bean dreg.

An appropriate amount of the conventional plant urease solution obtained is weighed and added to each of multiple beakers, and a pretreatment reagent is added to the beakers at different concentrations. In the present invention, calcium chloride is used as the pretreatment reagent. A resulting solution is stirred for 5 min and then centrifuged for 15 min at 4° C. and 3,000 r/min with a KDC-2046 low-speed refrigerated centrifuge to obtain a resulting mixture; and the resulting mixture after centrifugation is filtered, and a filtrate and a solid residue are collected, separately, wherein the filtrate is a pretreated plant urease solution and the solid residue refers to organic matters such as soybean protein.

The pretreated plant urease solutions of different pretreatment plans are sorted according to numbers of the beakers. A biuret staining method is used to test a protein content for each pretreated plant urease solution, and a conductivity method is used to test the urease activity for each pretreated plant urease solution. With each of an activity residual rate S and a protein utilization rate K for a pretreated plant urease solution as y-coordinate and a concentration of the pretreatment reagent as x-coordinate, curves are plotted; S and K values are comprehensively analyzed, and the optimal pretreatment reagent concentration is selected according to a selection principle, which is the optimal pretreatment plan; and a pretreated plant urease solution obtained from the optimal pretreatment plan is the optimal pretreated plant urease solution at the concentration.

A 0.1 to 3 mol/L of urea solution is mixed with a 0.1 to 3 mol/L of calcium salt solution in equal volumes, and a resulting mixture is thoroughly stirred to obtain an inorganic treatment solution. The optimal pretreated plant urease solution is mixed with the inorganic treatment solution in a volume ratio of 4:1 to 1:4, and a resulting mixture is thoroughly stirred to obtain the soil solidification agent.

The bean dreg A is dissolved with 10 L of deionized water, and a resulting mixture is stirred with a magnetic mixer for 30 to 40 min and filtered through a prewetted white gauze; the white gauze is vigorously squeezed to collect a filtrate as much as possible, which is a soybean protein solution A; and a filter residue is collected, which is a bean dreg B.

The solid residue B is dissolved with 10 L of deionized water, a resulting mixture is stirred with a magnetic mixer for 1 to 3 h until the solid residue is almost completely dissolved, and the stirring is stopped; and a resulting solution is filtered, and a filtrate is collected, which is a soybean protein solution B.

The soybean protein solution A and the soybean protein solution B are mixed to obtain a soybean protein solution C, and the soybean protein solution C involves the protein that can be reused throughout the process, which can be made into tofu, dried tofu, and other by-products by conventional production processes. Finally, the bean dreg B can be made into bean meal by a conventional production process.

Examples of urease activity test for plant urease solutions with different bean powder contents are provided below.

TABLE 1

Addition amount and concentration of bean powder in each example.

| | Bean powder mass (g) | Bean powder concentration (g/L) | Pretreatment reagent |
|---|---|---|---|
| Example 1 | 400 | 40 | calcium chloride |
| Example 2 | 800 | 80 | calcium chloride |
| Example 3 | 1200 | 120 | calcium chloride |
| Example 4 | 1600 | 160 | calcium chloride |
| Example 5 | 400 | 40 | magnesium chloride |
| Example 6 | 400 | 40 | calcium sulfate |

Example 1

8 small beakers (250 mL) were prepared, 100 mL of a conventional plant urease solution (40 g/L) was taken and added to each of the 8 beakers, and the beakers were numbered 1 to 8.0 g, 0.022 g, 0.044 g, 0.066 g, 0.1 g, 0.133 g, 0.166 g, and 0.222 g of an anhydrous calcium chloride solid (analytically pure) were added to the 8 beakers, respectively, such that the pretreatment reagents in the 8 beakers had concentrations of 0 mol/L, 0.002 mol/L, 0.004 mol/L, 0.006 mol/L, 0.009 mol/L, 0.012 mol/L, 0.015 mol/L, and 0.020 mol/L, respectively.

Figure 1:
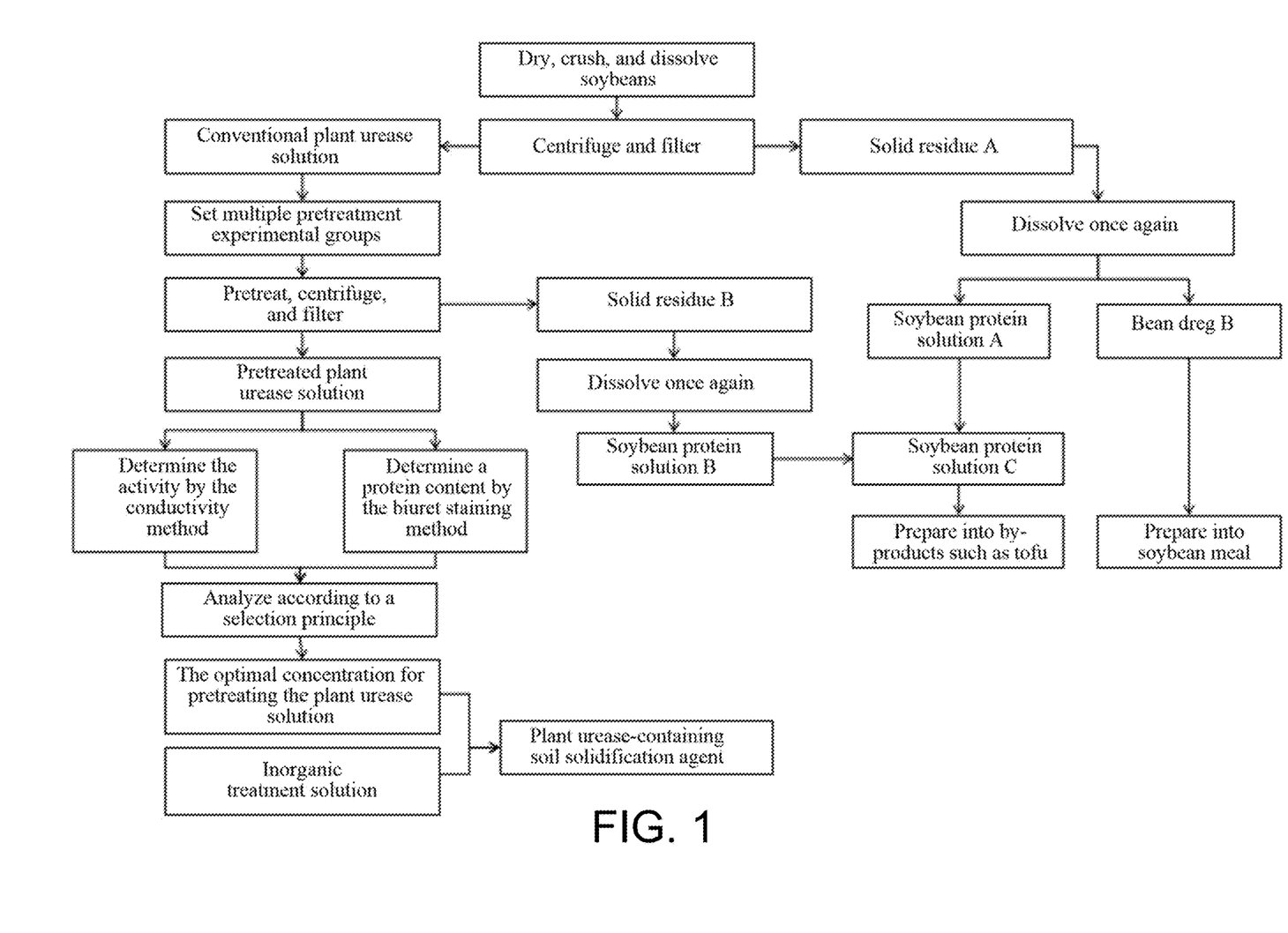
FIG. 1 is a flow chart of a zero-waste production process of a plant urease-containing soil solidification agent.
Figure 2:
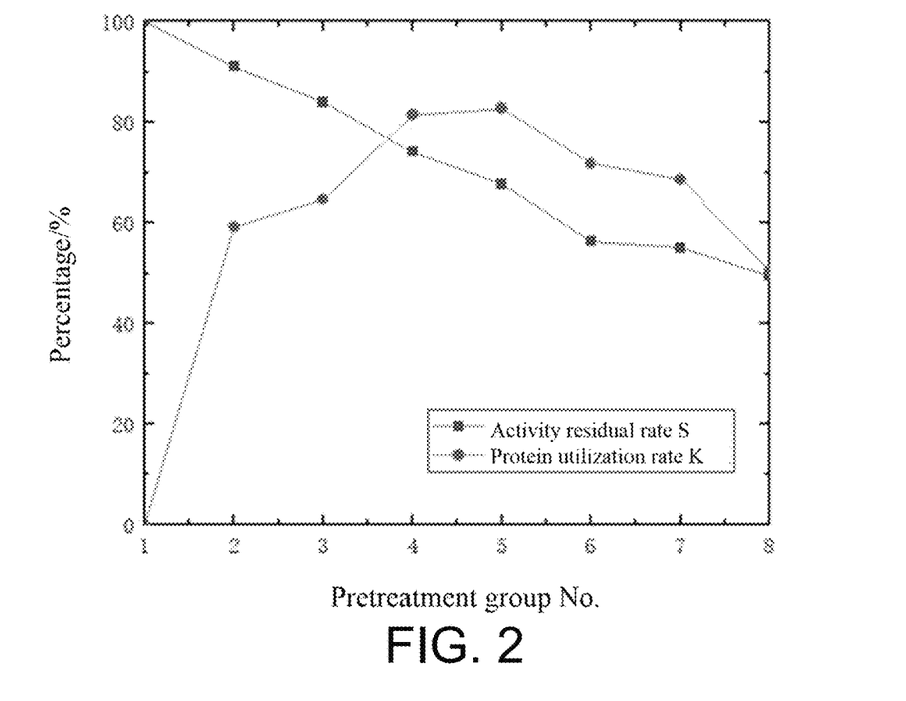
FIG. 2 shows S/K curves for a 40 g/L of plant urease solution pretreated with calcium chloride.

Test results of urease activity and protein concentration were shown in FIG. 2.

TABLE 2

| S/K values for 40 g/L plant urease solutions pretreated with calcium chloride | | | | | | | | |
|---|---|---|---|---|---|---|---|---|
| No. | 1 | 2 | 3 | 4 | 5 | 6 | 7 | 8 |
| S | 100.00% | 91.13% | 84.05% | 74.19% | 67.74% | 56.36% | 55.11% | 49.55% |
| K | 0.00% | 59.21% | 64.70% | 81.49% | 82.77% | 71.88% | 68.63% | 60.50% |

The results in FIG. 2 and Table 2 were analyzed, and it can be known that, for the 40 g/L of plant urease solution, the experimental plan of the experimental group 4 was the optimal pretreatment plan, in which case, 0.666 g of analytically pure anhydrous calcium chloride needs to be added to per liter of the conventional plant urease solution. The required conventional plant urease solution was pretreated according to this pretreatment plan. Preparation of an inorganic treatment solution: a 0.6 mol/L of urea solution was mixed with a 0.6 mol/L of calcium salt solution in equal volumes, and a resulting mixture was thoroughly stirred to obtain the inorganic treatment solution. Preparation of a soil solidification agent: the pretreated plant urease solution was mixed with the inorganic treatment solution in a volume ratio of 1:1, and a resulting mixture was thoroughly stirred to obtain the soil solidification agent.

Example 2

8 small beakers (250 mL) were prepared, 100 mL of a conventional plant urease solution (40 g/L) was taken and added to each of the 8 beakers, and the beakers were numbered 1 to 8. 0.0 g, 0.044 g, 0.088 g, 0.133 g, 0.178 g, 0.222 g, 0.266 g, and 0.311 g of an anhydrous calcium chloride solid (analytically pure) were added to the 8 beakers, respectively, such that the pretreatment reagents in the 8 beakers had concentrations of 0 mol/L, 0.004 mol/L, 0.008 mol/L, 0.012 mol/L, 0.016 mol/L, 0.020 mol/L, 0.024 mol/L, and 0.028 mol/L, respectively.

Figure 3:
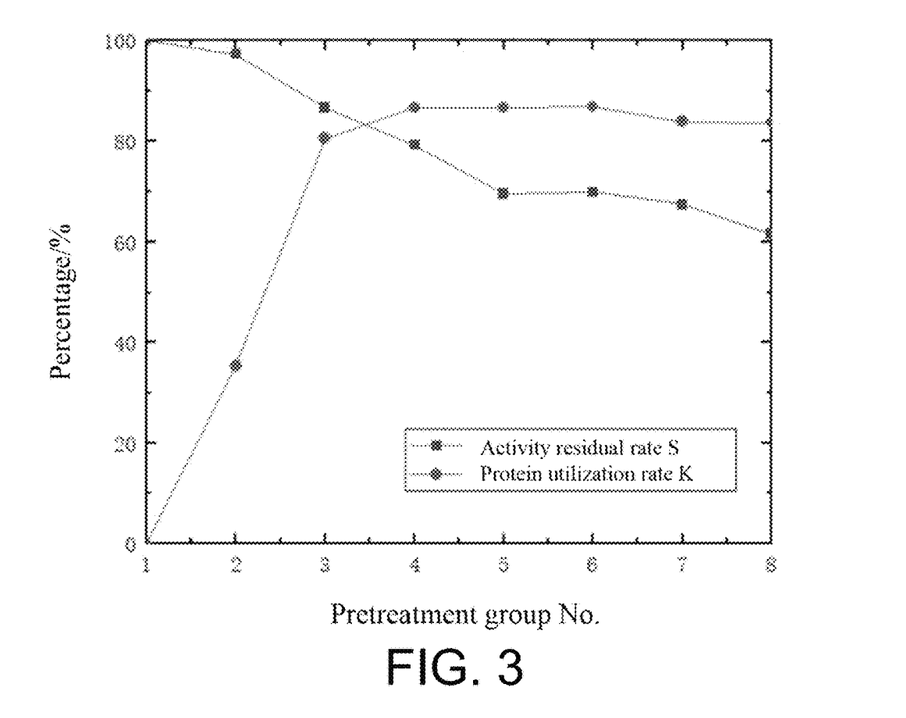
FIG. 3 shows S/K curves for an 80 g/L of plant urease solution pretreated with calcium chloride.

Test results of urease activity and protein concentration were shown in FIG. 3.

TABLE 3

S/K values for 80 g/L plant urease solutions pretreated with calcium chloride

| No. | 1 | 2 | 3 | 4 | 5 | 6 | 7 | 8 |
|---|---|---|---|---|---|---|---|---|
| S | 100.00% | 97.27% | 86.67% | 79.24% | 69.50% | 69.90% | 67.42% | 61.57% |
| K | 0.00% | 35.33% | 80.60% | 86.63% | 86.67% | 86.92% | 83.87% | 83.67% |

The results in FIG. 3 and Table 3 were analyzed, and it can be known that, for the 80 g/L of plant urease solution, the experimental plan of the experimental group 4 was the optimal pretreatment plan, in which case, 1.332 g of analytically pure anhydrous calcium chloride needs to be added to per liter of the conventional plant urease solution. The required conventional plant urease solution was pretreated according to this pretreatment plan. Preparation of an inorganic treatment solution: a 1.2 mol/L of urea solution was mixed with a 1.2 mol/L of calcium salt solution in equal volumes, and a resulting mixture was thoroughly stirred to obtain the inorganic treatment solution. Preparation of a soil solidification agent: the pretreated plant urease solution was mixed with the inorganic treatment solution in a volume ratio of 1:1, and a resulting mixture was thoroughly stirred to obtain the soil solidification agent.

Example 3

8 small beakers (250 mL) were prepared, 100 mL of a conventional plant urease solution (120 g/L) was taken and added to each of the 8 beakers, and the beakers were numbered 1 to 8. 0.0 g, 0.0666 g, 0.133 g, 0.2 g, 0.266 g, 0.333 g, 0.4 g, and 0.466 g of an anhydrous calcium chloride solid (analytically pure) were added to the 8 beakers, respectively, such that the pretreatment reagents in the 8 beakers had concentrations of 0 mol/L, 0.006 mol/L, 0.012 mol/L, 0.018 mol/L, 0.024 mol/L, 0.030 mol/L, 0.036 mol/L, and 0.042 mol/L, respectively.

Figure 4:
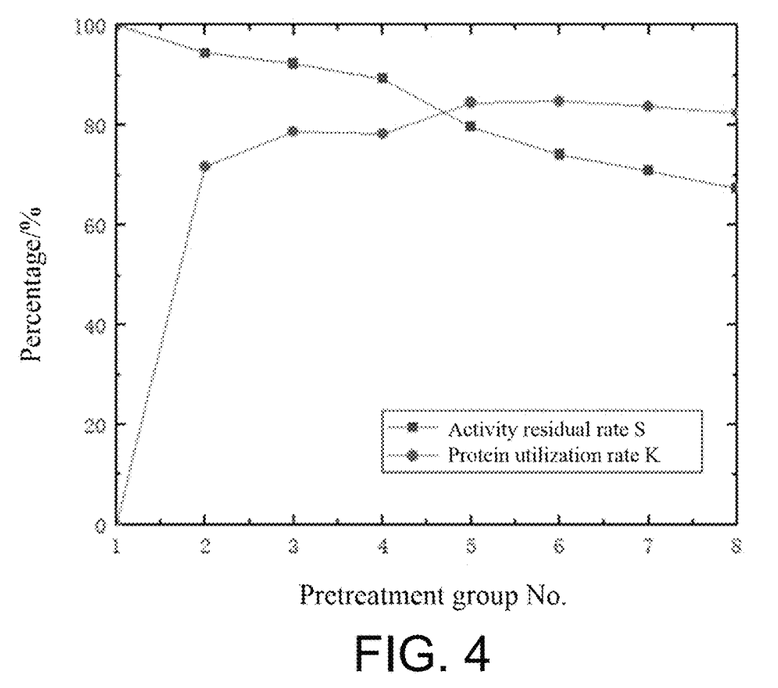
FIG. 4 shows S/K curves for a 120 g/L of plant urease solution pretreated with calcium chloride.

Test results of urease activity and protein concentration were shown in FIG. 4.

TABLE 4

S/K values for 120 g/L plant urease solutions pretreated with calcium chloride

| No. | 1 | 2 | 3 | 4 | 5 | 6 | 7 | 8 |
|---|---|---|---|---|---|---|---|---|
| S | 100.00% | 94.57% | 92.39% | 89.41% | 79.70% | 74.10% | 70.95% | 67.34% |
| K | 0.00% | 71.74% | 78.74% | 78.35% | 84.54% | 84.84% | 83.83% | 82.51% |

The results in FIG. 4 and Table 4 were analyzed, and it can be known that, for the 120 g/L of plant urease solution, the experimental plan of the experimental group 6 was the optimal pretreatment plan, in which case, 3.329 g of analytically pure anhydrous calcium chloride needs to be added to per liter of the conventional plant urease solution. The required conventional plant urease solution was pretreated according to this pretreatment plan. Preparation of an inorganic treatment solution: a 1.8 mol/L of urea solution was mixed with a 1.8 mol/L of calcium salt solution in equal volumes, and a resulting mixture was thoroughly stirred to obtain the inorganic treatment solution.

Example 4

7 small beakers (250 mL) were prepared, 100 mL of a conventional plant urease solution (160 g/L) was taken and added to each of the 7 beakers, and the beakers were numbered 1 to 7. 0 g, 0.089 g, 0.178 g, 0.266 g, 0.355 g, 0.444 g, and 0.533 g of an anhydrous calcium chloride solid (analytically pure) were added to the 7 beakers, respectively, such that the pretreatment reagents in the 7 beakers had concentrations of 0 mol/L, 0.008 mol/L, 0.016 mol/L, 0.024 mol/L, 0.032 mol/L, 0.040 mol/L, and 0.048 mol/L, respectively.

Figure 5:
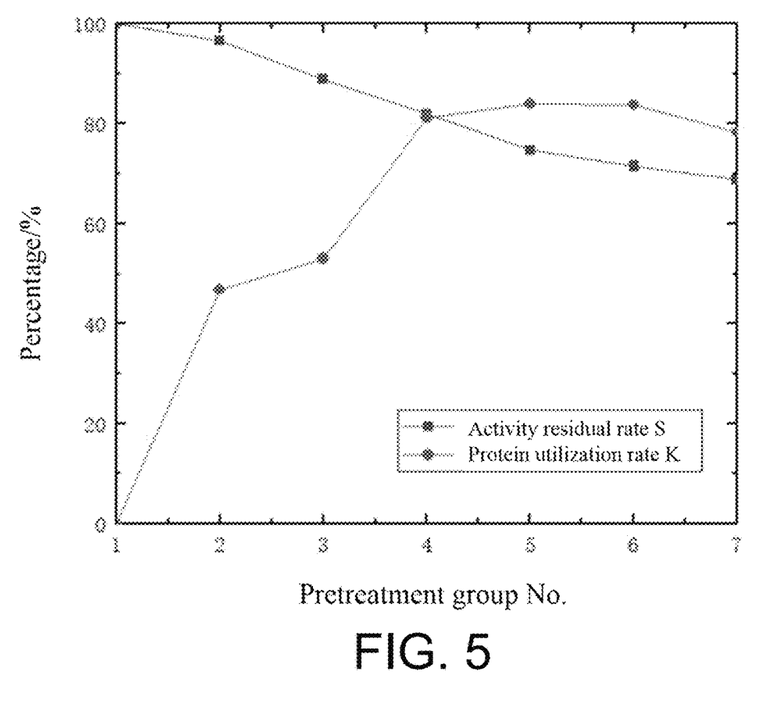
FIG. 5 shows S/K curves for a 160 g/L of plant urease solution pretreated with calcium chloride.

Test results of urease activity and protein concentration were shown in FIG. 5.

TABLE 5

S/K values for 160 g/L plant urease solutions pretreated with calcium chloride

| No. | 1 | 2 | 3 | 4 | 5 | 6 | 7 |
|---|---|---|---|---|---|---|---|
| S | 100.00% | 96.64% | 88.97% | 81.98% | 74.74% | 71.50% | 68.83% |
| K | 0.00% | 46.83% | 53.08% | 81.24% | 84.08% | 83.85% | 78.30% |

The results in FIG. 5 and Table 5 were analyzed, and it can be known that, for the 160 g/L of plant urease solution, the experimental plan of the experimental group 5 was the optimal pretreatment plan, in which case, 3.551 g of analytically pure anhydrous calcium chloride needs to be added to per liter of the conventional plant urease solution. The required conventional plant urease solution was pretreated according to this pretreatment plan. Preparation of an inorganic treatment solution: a 2.4 mol/L of urea solution was mixed with a 2.4 mol/L of calcium salt solution in equal volumes, and a resulting mixture was thoroughly stirred to obtain the inorganic treatment solution. Preparation of a soil solidification agent: the pretreated plant urease solution was mixed with the inorganic treatment solution in a volume ratio of 1:1, and a resulting mixture was thoroughly stirred to obtain the soil solidification agent.

Example 5

8 small beakers (250 mL) were prepared, 100 mL of a conventional plant urease solution (40 g/L) was taken and added to each of the 8 beakers, and the beakers were numbered 1 to 8. 0 g, 0.019 g, 0.038 g, 0.057 g, 0.0855 g, 0.114 g, 0.143 g, and 0.19 g of a magnesium chloride hexahydrate solid (analytically pure) were added to the 8 beakers, respectively, such that the pretreatment reagents in the 8 beakers had concentrations of 0 mol/L, 0.002 mol/L, 0.004 mol/L, 0.006 mol/L, 0.009 mol/L, 0.012 mol/L, 0.015 mol/L, and 0.020 mol/L, respectively.

Figure 6:
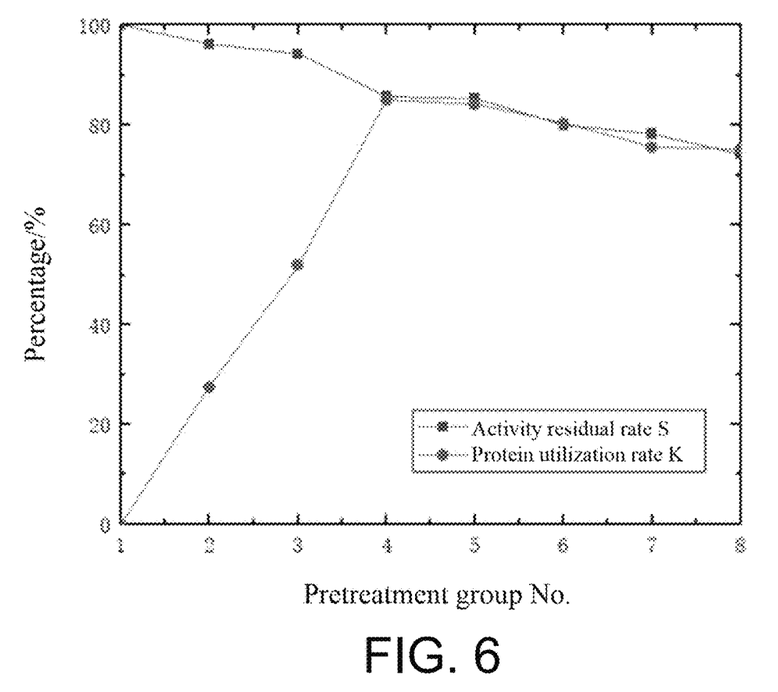
FIG. 6 shows S/K curves for a 40 g/L of plant urease solution pretreated with magnesium chloride.

Test results of urease activity and protein concentration were shown in FIG. 6.

TABLE 6

S/K values for 40 g/L plant urease solutions pretreated with magnesium chloride

| No. | 1 | 2 | 3 | 4 | 5 | 6 | 7 | 8 |
|---|---|---|---|---|---|---|---|---|
| S | 100.00% | 96.31% | 94.29% | 85.79% | 85.36% | 80.07% | 78.31% | 74.19% |
| K | 0.00% | 27.40% | 52.01% | 85.07% | 84.14% | 80.46% | 75.60% | 75.33% |

The results in FIG. 6 and Table 6 were analyzed, and it can be known that, for the 40 g/L of plant urease solution, the experimental plan of the experimental group 4 was the optimal pretreatment plan, in which case, 0.57 g of analytically pure magnesium chloride hexahydrate needs to be added to per liter of the conventional plant urease solution. The required conventional plant urease solution was pretreated according to this pretreatment plan. Preparation of an inorganic treatment solution: a 0.6 mol/L of urea solution was mixed with a 0.6 mol/L of calcium salt solution in equal volumes, and a resulting mixture was thoroughly stirred to obtain the inorganic treatment solution. Preparation of a soil solidification agent: the pretreated plant urease solution was mixed with the inorganic treatment solution in a volume ratio of 1:1, and a resulting mixture was thoroughly stirred to obtain the soil solidification agent.

Example 6

8 small beakers (250 mL) were prepared, 100 mL of a conventional plant urease solution (40 g/L) was taken and added to each of the 8 beakers, and the beakers were numbered 1 to 8. 0 g, 0.027 g, 0.054 g, 0.082 g, 0.122 g, 0.163 g, 0.204 g, and 0.272 g of an analytically pure calcium sulfate solid were added to the 8 beakers, respectively, such that the pretreatment reagents in the 8 beakers had concentrations of 0 mol/L, 0.002 mol/L, 0.004 mol/L, 0.006 mol/L, 0.009 mol/L, 0.012 mol/L, 0.015 mol/L, and 0.020 mol/L, respectively.

Figure 7:
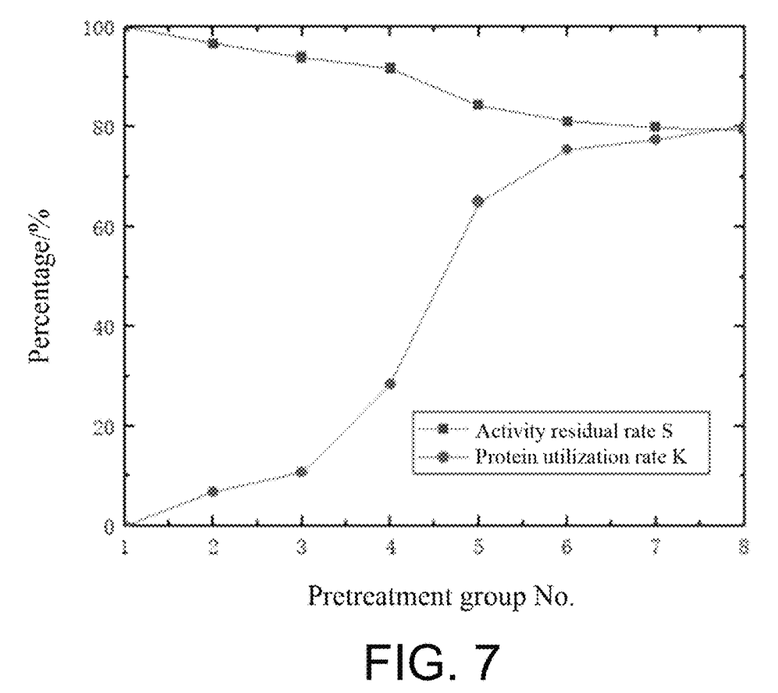
FIG. 7 shows S/K curves for a 40 g/L of plant urease solution pretreated with calcium sulfate.

Test results of urease activity and protein concentration were shown in FIG. 7.

TABLE 7

S/K values for 40 g/L plant urease solutions pretreated with calcium sulfate

| No. | 1 | 2 | 3 | 4 | 5 | 6 | 7 | 8 |
|---|---|---|---|---|---|---|---|---|
| S | 100.00% | 96.72% | 93.91% | 91.75% | 84.35% | 81.07% | 79.94% | 79.48% |
| K | 0.00% | 6.80% | 10.74% | 28.33% | 64.97% | 75.46% | 77.41% | 80.33% |

The results in FIG. 7 and Table 7 were analyzed, and it can be known that, for the 40 g/L of plant urease solution, the experimental plan of the experimental group 8 was the optimal pretreatment plan, in which case, 2.72 g of analytically pure calcium sulfate needs to be added to per liter of the conventional plant urease solution. The required conventional plant urease solution was pretreated according to this pretreatment plan. Preparation of an inorganic treatment solution: a 0.6 mol/L of urea solution was mixed with a 0.6 mol/L of calcium salt solution in equal volumes, and a resulting mixture was thoroughly stirred to obtain the inorganic treatment solution. Preparation of a soil solidification agent: the pretreated plant urease solution was mixed with the inorganic treatment solution in a volume ratio of 1:1, and a resulting mixture was thoroughly stirred to obtain the soil solidification agent.

Implementation examples related to soil solidification according to the present invention are provided below.

Example 7

A traditional soil solidification method usually uses a solidification agent containing a conventional urease solution for soil solidification. Effective ingredients in such a solidification agent include plant urease, a calcium salt, and urea, wherein urease catalyzes the decomposition of urea to in situ produce carbonate ions in soil, and carbonate ions react with the calcium salt to form calcium carbonate with cementing capacity, which makes loosen soil particles cemented together, thereby achieving the purpose of soil solidification. However, due to the limitation of crude purification, it is difficult to effectively separate out some ineffective ingredients when plant urease is extracted from a plant raw material, which makes a traditional soil solidification agent generally have low purity, many impurities, and other routine problems. Impurities in the traditional soil solidification agent mainly include small molecule proteins, lipids, etc., wherein the small molecule proteins show the greatest impact on a soil solidification effect. Under the action of an external strong electrolyte, the stable ionization balance of small molecule proteins is broken, such that coagulation occurs and large molecule proteins are formed. Large molecule proteins can block voids among soil particles and prevent effective ingredients of a soil solidification agent from penetrating into soil, thereby resulting in poor soil solidification. Therefore, the traditional soil solidification method is limited by many aspects such as the number of treatments and the treatment concentration, which is also a common challenge faced by the traditional soil solidification method using a soil solidification agent.

The present invention improves the traditional soil solidification agent, wherein impurities in the traditional soil solidification agent are selectively separated and removed. That is, most of small molecule proteins are effectively separated out with no influence or little influence on the effective ingredients for soil solidification, such that an improved soil solidification agent has higher purity and better effect. Due to the separation and removal of most small molecule proteins, voids among soil particles will not be blocked during a soil solidification process, the soil solidification effect is prominent, and a soil solidification plan can also be a multi-treatment and high-concentration treatment plan.

In this example, with a low-concentration and multi-spraying plan (a 40 g/L of plant urease solution was sprayed 4 times), a sand-fixation test was performed on different test sites to compare and analyze the soil solidification effects of the traditional method and the method of the present invention. After the treatment was completed, a surface state of a sample was observed, and a bearing capacity test was performed on a surface of a solidified sample with a foundation bearing capacity tester. Final results were subjected to comparative analysis to further confirm the superiority of the present invention.

Figure 8A:
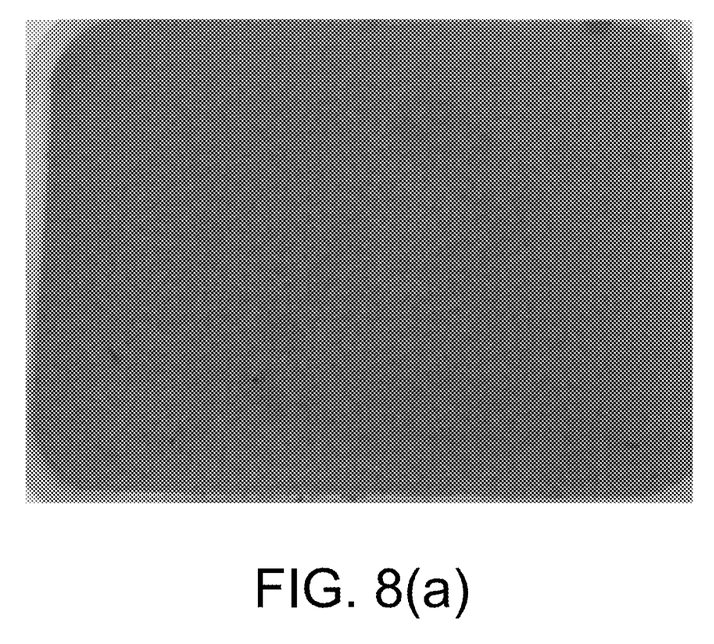
Figure 8B:
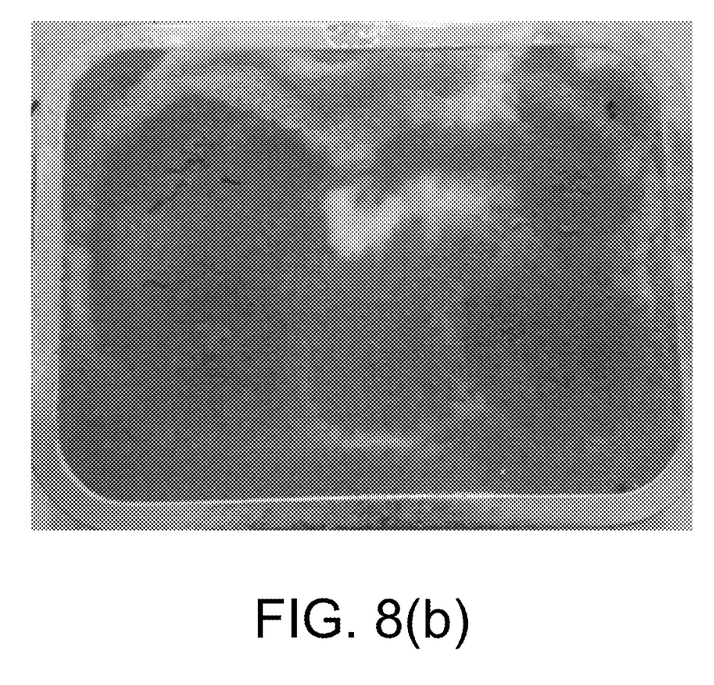

FIG. 8 is a comparison diagram of surface states of the samples sprayed with the two soil solidification agents twice. It can be seen from the figure that, after the traditional soil solidification agent was sprayed twice, effusion occurred locally on the surface of sand, and a specified amount of white substance was accumulated; and after the pretreated plant urease-containing soil solidification agent was sprayed twice, there was no effusion on the surface of sand, and there was also no white foamy substance. As the traditional soil solidification agent had a large amount of small molecular proteins and calcium salts, after the traditional soil solidification agent was sprayed on sand, the ionization balance of these small molecule proteins was broken, and these small molecule proteins aggregated into large molecule proteins to block some voids in sand, which resulted in a reduced infiltration rate of the soil solidification agent. Therefore, after the traditional soil solidification agent was sprayed twice, effusion occurred locally on a sand surface, and a white substance (namely, large molecule proteins in situ generated on the sand surface) was accumulated on the sand surface. As the pretreated plant urease-containing soil solidification agent only had a small amount of small molecule proteins, after the ionization balance was broken, only a small amount of large molecule proteins was produced, such that most of soil voids were not blocked. Therefore, after the pretreated plant urease-containing soil solidification agent was sprayed twice, voids in soil were not blocked, the soil solidification agent could infiltrate normally, and no effusion and large molecule proteins occurred on the sand surface.

Figure 9A:
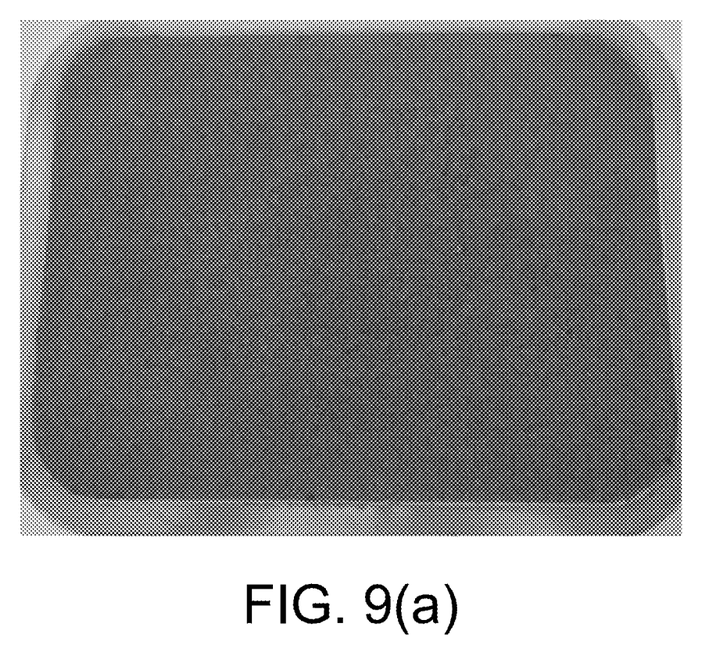
Figure 9B:
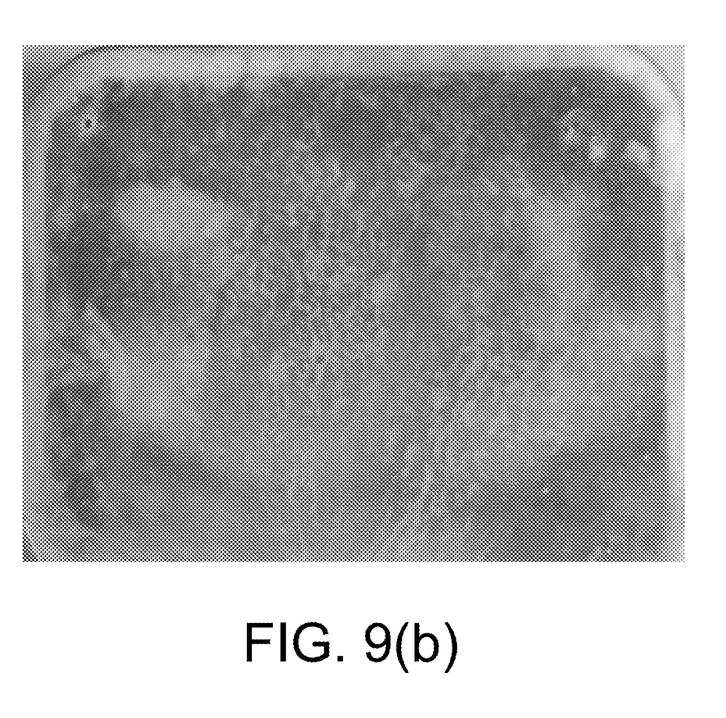

FIG. 9 is a comparison diagram of surface states of the samples sprayed with the two soil solidification agents 4 times. It can be seen from the figure that, after the traditional soil solidification agent was sprayed four times, a sand surface was almost completely covered with effusion, and the infiltration rate was significantly reduced; and after the pretreated plant urease-containing soil solidification agent was sprayed four times, there was still no effusion on a sand surface, only the infiltration rate of the solution was slightly reduced (which did not affect the complete infiltration of the solution), and there was no white foamy substance on a surface of a sample. As the traditional soil solidification agent had a large amount of small molecule proteins and calcium salts, after the traditional soil solidification agent was sprayed on sand, the ionization balance of these small molecule proteins was broken, and these small molecule proteins aggregated into large molecule proteins to block some voids in the sand. With the increase in the number of soil treatments, voids among soil particles were almost completely blocked, and the traditional soil solidification agent could hardly infiltrate, so the sand surface was almost completely covered with effusion. As the pretreated plant urease-containing soil solidification agent only had a small amount of small molecule proteins, after the ionization balance was broken, only a small amount of large molecule proteins was produced, such that most soil voids were not blocked. With the increase in the number of treatments, voids among soil particles were partially blocked (resulting in a reduced infiltration rate of the soil solidification agent), but most voids still existed, so the soil solidification agent could finally infiltrate completely. Moreover, because a small molecule protein content in the pretreated plant urease-containing soil solidification agent was very small, visible large molecule proteins could not be formed on a sand surface, so there was no white foamy substance on a surface of a sample.

Figure 10:
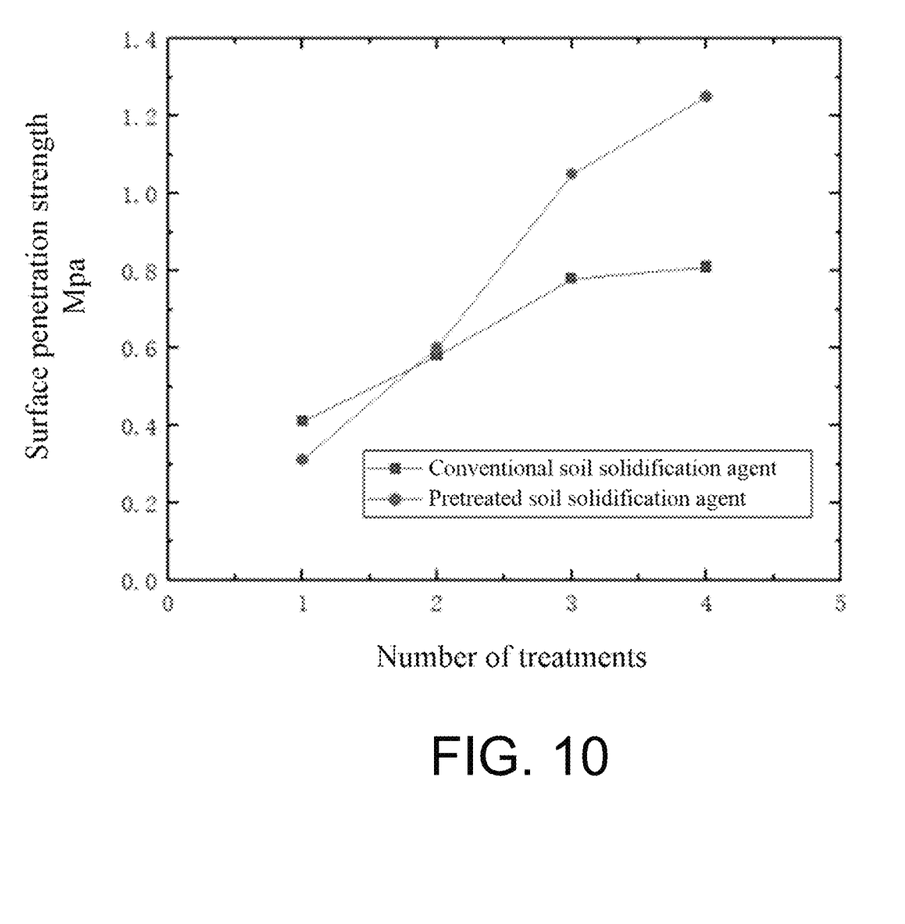
FIG. 10 shows the comparison of penetration strength between a conventional soil solidification agent and the pretreated soil solidification agent in multiple treatments.

FIG. 10 shows the comparison of penetration strength between a conventional soil solidification agent and the pretreated soil solidification agent in multiple treatments. It can be seen that, in a single treatment, the soil treated with the conventional soil solidification agent had a higher strength than the soil treated with the pretreated plant urease-containing soil solidification agent. This is because proteins in the pretreated plant urease-containing soil solidification agent were largely removed. After small molecule proteins aggregated into large molecule proteins, the large molecule proteins, together with formed calcium carbonate crystals, filled voids among soil particles, thereby playing the roles of structural support and cementation and providing a part of the penetration strength. Therefore, for a single treatment, the traditional method exhibited a better solidification effect than the method of the present invention. However, the protein can only provide a limited strength, and the protein is an organic matter and will be decomposed over time, resulting in insufficient durability of soil solidification. With the increase in the number of treatments, the pretreated soil solidification agent finally led to a soil strength higher than that of the traditional soil solidification agent. Because a large amount of protein in the traditional soil solidification agent blocked voids among soil particles and the clogging degree for voids increased with the increase in the number of treatments, the traditional soil solidification agent could not effectively infiltrate to a soil location to be solidified subsequently, such that an expected amount of calcium carbonate could not be generated in a target location, resulting in poor strength enhancement. As proteins were effectively separated and removed in the pretreated soil solidification agent, an expected amount of calcium carbonate crystal could be generated at a target soil location with the increase in the number of treatments, so the solidification strength of soil increased with the increase in the number of treatments.

Example 8

The present invention was adopted for wind-break and sand-fixation, and a 160 g/L of plant urease solution was expected to be used. According to Example 4, a 0.024 mol/L of pretreatment plan was used to pretreat the conventional plant urease solution. A 2.4 mol/L of urea solution was mixed with a 2.4 mol/L of calcium salt solution in equal volumes, and a resulting mixture was thoroughly stirred to obtain an inorganic treatment solution. A pretreated plant urease solution was mixed with the inorganic treatment solution in a volume ratio of 1:1, and a resulting mixture was thoroughly mixed to obtain a soil solidification agent.

According to a spraying plan of 4 L/m$^2$, the soil solidification agent was sprayed into a sand to be solidified. According to the operation in step 5, a soybean protein solution was made into tofu, and a bean dreg was made into soybean meal. In combination with local prices of an experimental site, costs of a conventional plant urease-containing solidification agent and a pretreated plant urease-containing solidification agent to treat the same area of sand were compared to analyze and evaluate the economic benefits of the present invention.

TABLE 8

Prices of experimental materials (all actual prices at the experimental site)

| Material name | Unit price | Specification |
|---|---|---|
| Anhydrous calcium chloride | 2.1 yuan | kg |
| Urea | 2.4 yuan | kg |
| Soybean | 4.6 yuan | kg |
| Tofu | 5 yuan | kg |
| Soybean meal | 3 yuan | kg |

TABLE 9

Cost of the conventional plant urease-containing solidification agent treatment plan

| Soybean (1 m$^2$) | Calcium chloride (1 m$^2$) | Urea (1 m$^2$) | By-product value (1 m$^2$) | Cost per m$^2$ of sand | Cost per mu of sand |
|---|---|---|---|---|---|
| 1.472 yuan | 0.746 yuan | 0.461 yuan | 0 yuan | 2.679 yuan | 1786 yuan |

TABLE 10

Cost of the pretreated plant urease-containing solidification agent treatment plan

| Soybean (1 m$^2$) | Calcium chloride (1 m$^2$) | Urea (1 m$^2$) | By-product value (1 m$^2$) | Cost per m$^2$ of sand | Cost per mu of sand |
|---|---|---|---|---|---|
| 1.472 yuan | 0.746 yuan | 0.461 yuan | −2.118 yuan | 0.561 yuan | 374 yuan |

The economic costs in Table 8 and Table 9 were compared, and it can be known that the present invention can reduce a raw material cost of wind-break and sand-fixation to about 20% of an initial cost, indicating significant economic benefits.

What is claimed is:

1. A process of a soil solidification using a plant urease-containing soil solidification agent, the plant urease-containing soil solidification agent is prepared from a pretreated plant urease solution and an inorganic treatment solution in a volume ratio of 4:1 to 1:4, the soil solidification is performed by spraying the soil solidification agent four times 4, wherein the inorganic treatment solution is a solution prepared by mixing a 0.1 to 3 mol/L of urea solution with a 0.1 to 3 mol/L of calcium salt solution in equal volumes to obtain a resulting mixture, and thoroughly stirring the resulting mixture, wherein a production process of the plant urease-containing soil solidification agent comprises the following steps:

step 1, preparation of a conventional plant urease solution:

drying beans in an oven at 60° C. for 2 h, crushing the dried beans in a crusher and sieving the crushed beans through a 100-mesh sieve to obtain a bean powder, and collecting and storing the bean powder at a ventilated place;

dissolving the bean powder in deionized water to obtain a first resulting mixture, and thoroughly stirring the first resulting mixture to obtain a 10 to 200 g/L of bean powder solution; centrifuging the bean powder solution for 15 min at 4° C. and 3,000 r/min with a KDC-2046 low-speed refrigerated centrifuge; and filtering the centrifuged bean powder solution to collect a solid residue A and a filtrate separately, wherein the filtrate is the conventional plant urease solution and the solid residue A is a bean dreg A;

step 2, pretreatment of the conventional plant urease solution:

refrigerating the conventional plant urease solution obtained in the step 1 for 12 h in a 5° C. environment, and taking the conventional plant urease solution out for later use before the pretreatment is performed; preparing a plurality of beakers, and numbering the beakers for later use; adding the conventional plant urease solution in an equal volume of 100 to 200 mL to each of the beakers, putting a magnetic rotor in each of the beakers, and placing the beakers on a magnetic stirrer for continuous stirring to ensure homogeneity of the conventional plant urease solution; taking a pretreatment reagent into an oven at 60° C. for 12 h to form agglomerates, and taking the agglomerates out from the oven and grinding the agglomerates into a powder for later use;

according to an initial concentration of the conventional plant urease solution, selecting a corresponding pretreatment reagent concentration gradient plan; adding the pretreatment reagent to each of the plurality of beakers, stirring a resulting solution at a low speed for 5 min, and stopping the magnetic stirrer to let the solution stand for 5 min; when the solution undergoes a stratification and an upper supernatant is clear, pouring the resulting solution into a centrifuge bottle, and centrifuging the resulting solution for 15 min at 4° C. and 3,000 r/min with a low-speed refrigerated centrifuge; filtering the resulting solution after centrifugation to collect a clear solution and a solid residue B separately, wherein the clear solution is the pretreated plant urease solution and the solid residue B is organic matters including a soybean protein separated;

wherein as the conventional plant urease solution prepared in the step 1 has a concentration of 10 to 200 g/L, the corresponding pretreatment reagent concentration gradient plan of 0.0005 to 0.15 mol/L is selected to pretreat the conventional plant urease solution, including the following steps: a pretreatment reagent concentration gradient of 0.0005 to 0.0075 mol/L is used for the conventional plant urease solution with a concentration of 10 g/L; and a pretreatment reagent concentration gradient of 0.01 to 0.15 mol/L is used for the conventional plant urease solution with a concentration of 200 g/L;

step 3, determination of a pretreatment plan for the conventional plant urease solution with a predetermined concentration:

collecting the clear pretreated plant urease solutions from multiple different pretreatment plans obtained in the step 2, and sorting the clear pretreated plant urease solutions according to numbers of the beakers; as performances of the clear pretreated plant urease solutions represent pretreatment effects of the multiple different pretreatment plans on the conventional plant urease solution with the predetermined concentration, determining parameters including activity and protein content for each of the clear pretreated plant urease solutions, and analyzing the pretreatment effects of the multiple different pretreatment plans to determine the pretreatment plan for the conventional plant urease solution with the predetermined concentration;

wherein determining the pretreatment plan for the conventional plant urease solution with the predetermined concentration includes:

testing each of the pretreated plant urease solutions, including:

performing a biuret staining method to test the protein content for each of the pretreated plant urease solutions, and performing a conductivity method to test the urease activity for each of the pretreated plant urease solutions;

analyzing test results statistically;

plotting curves with each of an activity residual rate S and a protein utilization rate K for each of the pretreated plant urease solutions as y-coordinate and an addition concentration of the pretreatment reagent as x-coordinate;

analyzing values of the activity residual rate S and the protein utilization rate K comprehensively; and selecting a pretreatment reagent concentration according to a selection principle in order to determine the pretreatment plan for the conventional plant urease solution with the predetermined concentration; and pretreating the conventional plant urease solution according to the pretreatment plan for the conventional plant urease solution with the predetermined concentration to obtain the pretreated plant urease solution; and step 4, preparation of the soil solidification agent:

preparation of an inorganic treatment solution: mixing a 0.1 to 3 mol/L of urea solution with a 0.1 to 3 mol/L of calcium salt solution in equal volumes to obtain a second resulting mixture, and thoroughly stirring the second resulting mixture to obtain the inorganic treatment solution; and preparation of the soil solidification agent: mixing the pretreated plant urease solution with the inorganic treatment solution in a volume ratio of 4:1 to 1:4 to obtain a third resulting mixture, and thoroughly stirring the third resulting mixture to obtain the soil solidification agent, wherein the beans in the step 1 are soybeans or sword beans, the pretreatment reagent in the step 2 is calcium chloride, magnesium chloride, or calcium sulfate, in the step 2, the pretreatment reagent concentration gradient is preset in order to determine the pretreatment plan for the conventional plant urease solution with the predetermined concentration in the step 3, wherein as a concentration gradient reference standard, a pretreatment reagent concentration gradient of $5\times10^{-5}$ mol/L to $7.5\times10^{-4}$ mol/L is used for a 1 g/L conventional plant urease solution, in the step 3, the activity residual rate S of the pretreated plant urease solution is a ratio of a residual activity of the pretreated plant urease solution to an initial activity of the conventional plant urease solution without pretreatment; and the protein utilization rate K of the pretreated plant urease solution is a ratio of a concentration of proteins separated from the pretreated plant urease solution that can be secondarily utilized to an initial protein concentration of the conventional plant urease solution without pretreatment, in the step 3, the selection principle comprises:

presetting pretreatment groups at different concentrations to plot active protein curves; and selecting a pretreatment group corresponding to a maximum of the protein utilization rate $K_{max}$ as the pretreatment plan based on the activity residual rate $S \geq 70\%$, the calcium salt in the step 4 is calcium chloride, calcium acetate, or calcium nitrate.

* * * * *